United States Patent [19]
Yip

[11] Patent Number: 4,898,824
[45] Date of Patent: Feb. 6, 1990

[54] CROSSLINKED POLYACRYLAMIDE-SULFHYDRYL POLYMER FOR IMMOBILIZATION OF BIOLOGICALLY ACTIVE SUBSTANCES

[75] Inventor: Kin-Fai Yip, Elkhart, Ind.

[73] Assignee: Miles Inc., Elkhart, Ind.

[21] Appl. No.: 939,904

[22] Filed: Dec. 9, 1986

[51] Int. Cl.$^4$ .................. C12N 11/08; C12N 11/06
[52] U.S. Cl. .................................. 435/180; 435/181
[58] Field of Search ............... 435/174, 177, 180, 181, 435/182

[56] References Cited

U.S. PATENT DOCUMENTS

| | | | |
|---|---|---|---|
| 3,666,733 | 5/1972 | Epton | 435/180 X |
| 3,775,253 | 11/1973 | Dieter et al. | 435/180 |
| 4,175,073 | 11/1979 | Carlsson et al. | 435/180 X |
| 4,737,258 | 4/1988 | Ogawa et al. | 428/479.3 |

OTHER PUBLICATIONS

Inman, J. K., Methods In Enzymology, vol. XXXIV, part B, Academic Press, N.Y., 1974, pp. 30–33, 42–45.

Primary Examiner—David M. Naff
Attorney, Agent, or Firm—Daniel W. Collins

[57] ABSTRACT

A water-insoluble, crosslinked polyacrylamide copolymer is prepared having recurring monomeric residues of acrylamide, bisacrylamide or analogs thereof, and N,N'-bisacrylylcystamine or analogs thereof. The crosslinked copolymer can be formed into discrete particles having crosslinking disulfide groups on their external surface which can be reduced to provide activated particles having exposed chemically active sulfhydryl groups. The activated polyacrylamide particles are free of residual amino and carboxylic acid groups and can be reacted with suitable haptens and other biologically active substances to provide insolubilized forms thereof.

12 Claims, 1 Drawing Sheet

CROSSLINKED POLYACRYLAMIDE-SULFHYDRYL POLYMER FOR IMMOBILIZATION OF BIOLOGICALLY ACTIVE SUBSTANCES

BACKGROUND OF THE INVENTION

The present invention relates to solid support materials for the immobilization of biologically active substances thereto. In particular, the present invention relates to crosslinked polyacrylamide derivatized with functional groups to which biologically active substances can be coupled.

The immobilization of biologically active substances onto solid support materials has become an important research and diagnostic tool in various areas of biotechnology. For example, synthesis and use of solid support materials, particularly crosslinked polymer supports, having chemical structures which are physiochemically compatible with the backbone structure of a peptide has been described for use in solid-phase peptide synthesis where techniques for coupling peptides to a polymer [Stahl, et al., *J. Amer. Chem. Soc.*, Vol. 101(18) p. 5383(1979)] and the crosslinking of various polymers [Varadarajan, et al., *Biopolymers*, Vol. 22, p. 839(1983)] using reverse-phase suspension polymerization in aqueous organic mixtures have been employed to obtain favorable swelling properties of such support materials in order to provide increased external and internal reaction sites bearing appropriate functional groups.

Various analytical test systems have also been described which employ solid support materials for the separation of bound and free forms of a labeled reagent in order to determine the amount of analyte present in a liquid test sample. For example, U.S. Pat. No. 4,200,436 discloses an immunoassay for the detection of antigen employing an immobilized form of the antigen to be measured which is prepared by chemically binding or physically adsorbing the antigen to solid supports or carrier materials, such as polysaccharides or plastics, according to methods known in the art. Similarly, U.S. Pat. No. 4,551,426 discloses a heterogeneous immunoassay employing an immobilized form of ouabain which is prepared by coupling ouabain, either directly or through a spacer arm such as a protein, polyamino acid, or synthetic linker, to a support material, such as beaded agarose, beaded dextran, polyacrylamide, or glass, according to methods known in the art.

Although various solid support materials are known in the art as heretofore described, polyacrylamide supports, such as crosslinked polyacrylamide gels, are particularly useful for the coupling of ligands or other biologically active substances thereto and possess a number of advantages such as low nonspecific adsorption of biological macromolecules, high chemical and thermal stability, and freedom from attack by enzymes. The structural network of crosslinked polyacrylamide gels consists mainly of segments of linear polyethylene with alternate backbone carbon atoms bearing primary amide groups which contribute to the hydrophilic character of polyacrylamide and to its low adsorption to macromolecules. Although linear polyacrylamide is water-soluble, insoluble gel networks are formed by including a bifunctional monomer in the polymerization reaction to produce crosslinkages.

In order to effectively couple a biologically active substance to such crosslinked polyacrylamide supports, it is necessary to introduce functional groups to provide reactive coupling sites. For example, crosslinked polyacrylamide [S. Hjerten and R. Mosbach, *Anal. Chem.* Vol. 3, p. 109(1962)] can be aminoethyl-derivatized [J. K. Inman and H. M. Dintzis, *Biochemistry*, Vol. 8, p. 4074(1969)] to introduce amine functional groups, or can be aminoethyldithio- or sulfhydryl-derivatized [J. K. Inman, *Methods in Enzymology*, Vol. 34B, p. 30(1974)] to introduce sulfhydryl functional groups.

However, such derivatized polyacrylamide support materials nevertheless contain residual amino and/or carboxylic acid groups which can result in undesirable interaction with ionic compounds and produce a gel with high buffering capacity. Such amine functional groups can also interact with amine-sensitive ligands to inactivate or decrease the binding capacity thereof to its corresponding binding partner. In particular, where the ligand coupled to an aminoethyl-derivatized polyacrylamide support is, for example, an amine-sensitive ligand such as a glycosylated peptide sequence, the ability of such ligand to bind to a corresponding antibody is substantially decreased.

Accordingly, it is an object of the present invention to provide a polyacrylamide support material derivatized with functional groups which do not nonspecifically interact with amine-sensitive ligands.

Further, it is an object of the present invention to provide a polyacrylamide support material having no residual amine or carboxyl functional groups which would otherwise interact with ionic compounds.

Another object of the present invention is to provide a polyacrylamide support material having a low buffering capacity.

SUMMARY OF THE INVENTION

The present invention provides a water-insoluble, crosslinked polyacrylamide-sulfhydryl copolymer comprising recurring monomeric structural units of the formulae:

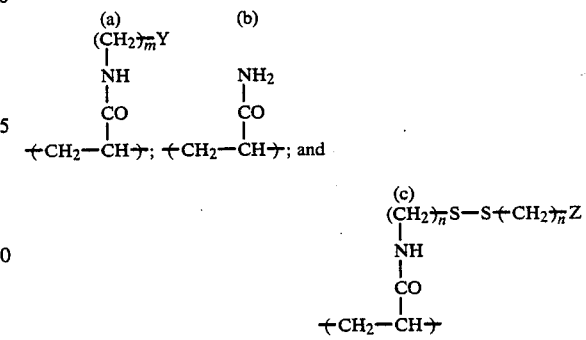

wherein a, b and c are randomly recurring monomeric structural units of a random polyacrylamide-sulfhydryl copolymer chain, m and n are, independently, integers from 1 through 6, preferably from 1 through 3 and from 2 through 4, respectively, and Y and Z are amide groups from other random polyacrylamide-sulfhydryl copolymer chains. The random copolymer chains are crosslinked to one another by the monomeric structural units a and c where Y and Z are amide groups from other such random copolymer chains to provide the crosslinked polyacrylamide-sulfhydryl copolymer of the present invention.

The crosslinked copolymer is generally in the form of discrete particles, preferably gel particles, and characterized by the external surface disulfide groups of the monomeric structural unit c. Such disulfide crosslinks can be reduced to provide chemically active sulfhydryl functional groups on the external surface which can be coupled to biologically active substances.

The present invention further provides a method for preparing the crosslinked polyacrylamide-sulfhydryl copolymer which comprises (i) copolymerizing a mixture comprising monomers of the formulae:

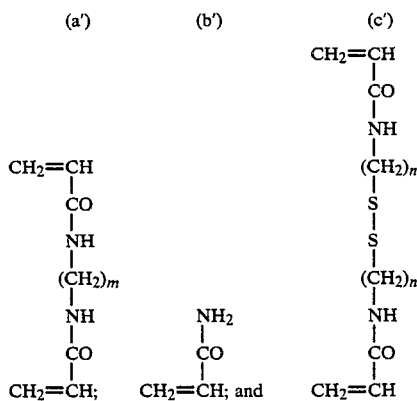

and (ii) isolating the crosslinked polyacrylamide-sulfhydryl copolymer of the present invention.

DESCRIPTION OF THE PREFERRED EMBODIMENTS

Figure 1:
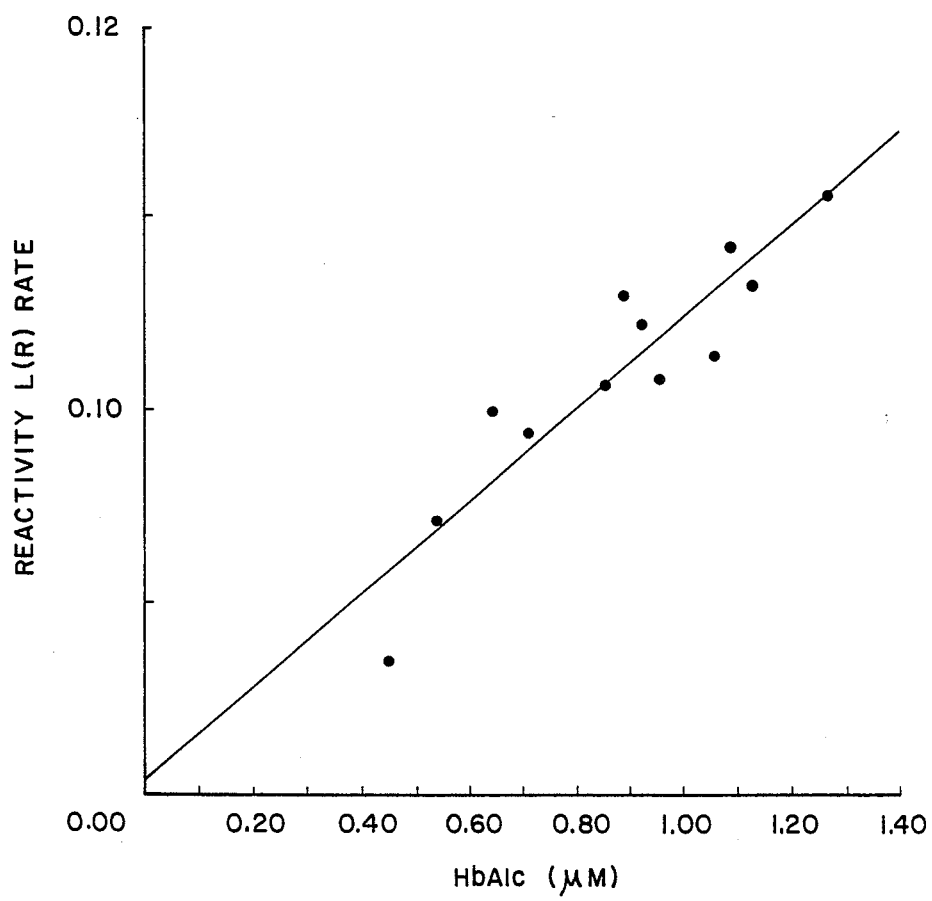
FIG. 1 is a graph which illustrates the reactivity of an immobilized glycopeptide reagent employing the polyacrylamide-sulfhydryl gel of the present invention in an immunoassay for the determination of the amount of glycopeptide from a liquid test sample.

The crosslinked polyacrylamide-sulfhydryl copolymer of the present invention is generally in the form of a solid matrix comprising the crosslinked random polyacrylamide-sulfhydryl copolymer chains which define internal and external surface areas. In particular, the random polyacrylamide-sulfhydryl copolymer chains comprise the monomeric residue structural units a, b and c, where b is an acrylamide residue, and which are distributed randomly along linear copolymer chains. The random copolymer chains are crosslinked to one another by the monomeric residue structural units a and c where Y and Z of the monomeric residue structural units a and c are amide groups from other such random copolymer chains.

The crosslinked copolymer is characterized by the disulfide group of the crosslinkage provided by the monomeric residue structural unit c which is present on both the internal and external surface areas of the crosslinked copolymer and which can be reduced with a reducing reagent to provide chemically active sulfhydryl functional groups. Such reduced form of the crosslinked copolymer is particularly useful as a solid support material in an immobilized reagent, which is more usually in the form of a gel or gel particle when in a liquid environment, such as that described in the copending U.S. patent application entitled "Stable Immobilized Hapten Reagent For Use In Heterogeneous Immunometric Assays" (U.S. Ser. No. 939,902), filed on even date herewith, where a biologically active substance can be covalently coupled to such external surface chemically active sulfhydryl functional groups, as will be described in greater detail hereinafter. A wide variety of biologically active substances are known which can be coupled to such chemically active sulfhydryl functional groups and include, but are not intended to be limited to, organic molecules, proteins, nucleic acids, and the like. In particular, biologically active substances such as haptens, antigens, antibodies, lectins, enzymes, receptor proteins, and ligands such as biotin, can be covalently coupled to such chemically active sulfhydryl functional groups to provide immobilized reagents thereof.

It is to be appreciated that where the crosslinked copolymer is employed as a solid support material in an immobilized reagent as heretofore described, it is desirable to covalently couple such biologically active substance substantially only to the external surface sulfhydryl functional groups. However, the crosslinked copolymer is highly hydrophilic and therefore exhibits an undesirable amount of swelling when in an aqueous liquid environment, usually from two- to three-fold greater in size. Such swelling permits the undesirable permeation and internalization of such biologically active substances or other reagents therein to result in the undesirable formation of covalent bonds between such biologically active substances and the sulfhydryl functional groups on the internal surface areas thereof. In retrospect, there is essentially no swelling of the crosslinked copolymer of the present invention when in the presence of a nonswelling liquid environment or solvent containing little or no water, preferably an organic solvent such as dimethylformamide, dimethylsulfoxide, acetone, chlorinated hydrocarbons, acyclic and cyclic alkylethers, and the like. Accordingly, the covalent binding of such biologically active substances is limited substantially only to the sulfhydryl functional groups on the external surface area of the crosslinked copolymer when in such nonswelling solvent which minimizes the permeation or internalization of such biologically active substances and other reagents into the crosslinked copolymer. It is also to be appreciated that such nonswollen crosslinked copolymer is also impervious to the reducing agent employed to reduce the disulfide groups to generate the chemically active sulfhydryl groups as heretofore described and, accordingly, limits the reduction thereof substantially only to the reduction of the disulfide groups on the external surface area of the crosslinked copolymer.

As will be described in greater detail hereinafter, the degree of swelling depends upon the ratio of monomeric structural units, the degree of crosslinking and crosslinking groups between the copolymer chains, and the monomeric compositions in the crosslinked copolymer. Preferably, the crosslinked copolymer comprises from between about 1% and 18% of the monomeric structural unit a, from between about 70% and 95% of the monomeric structural unit b, and from between about 2% and 12% of the monomeric structural unit c. More preferably, the crosslinked copolymer comprises from between about 2% and 16% of the monomeric structural unit a, from between about 80% and 94% of the monomeric structural unit b, and from between about 2% and 10% of the monomeric structural unit c.

Although various monomers can be selected by one skilled in the art to provide monomeric structural units a and c where m and n are defined as previously described, bisacrylamide (monomeric structural unit a)

and N,N'-bisacrylylcystamine (moneric structural unit c) residues are particularly preferred, where m is 1 and n is 2, respectively, which provide the crosslinkages between the random polyacrylamide-sulfhydryl copolymer chains as heretofore described. Preferably, such crosslinked copolymer comprises 88% or 94% of acrylamide residues, 10% or 2% of bis acrylamide (monomeric residue structural unit a), and 2% or 4% of N,N'-bisacrylylcystamine residues, respectively.

The crosslinked copolymer is generally in the form of a bulk polymer which can be reduced in size to discrete, irregularly shaped particles having increased external surface areas, generally into a slurry comprising gelatinous particles, according to methods known in the art, such as with a mechanical blender or homogenizer. The resulting particles, or gel particles, possess the same physical and chemical properties of the crosslinked copolymer as heretofore described to provide a variety of sizes which can be separated according to their respective sizes on a meshing screen having a predetermined mesh size. Preferably, the crosslinked copolymer of the present invention is homogenized and separated into particles from between about 20 82 m and 200 $\mu$m in diameter, preferably from between about 38 $\mu$m and 150 $\mu$m in diameter, and employed as a solid support material in an immobilized reagent as heretofore described.

For example, such crosslinked copolymer particles can be employed to prepare an immobilized glycopeptide reagent comprising the glycosylated N-terminal peptide sequence in the beta-subunit of human hemoglobin (i.e., glycopeptide) covalently linked to the sulfhydryl groups on the external surface of the copolymer matrix, such as described in the copending U.S. patent application entitled "Stable Immobilized Hapten Reagent For Use In Heterogeneous Immunometric Assays" described above. In particular, the glycopeptide is first activated by a bifunctional compound such as bismaleimide (1,1'-[methylenedi-4,1-phenylene]bismaleimide), bismaleimido-hexane, or bismaleimido-hexaethyleneglycol, and then reacted with the reduced form of the crosslinked copolymer of the present invention in the presence of the nonswelling solvent as heretofore described. It is to be appreciated that the nonswollen character of the crosslinked copolymer particle prevents the permeation and internalization of the glycopeptide and other reagents and, accordingly, excludes the glycopeptide from the internal surface thereof to thereby limit the covalent binding of the glycopeptide substantially only to the external surface sulfhydryl functional groups.

It is to be appreciated that the crosslinked polyacrylamide-sulfhydryl copolymer of the present invention does not contain residual amino or carboxylic acid groups which would otherwise interact with ionic compounds to result in the nonspecific binding thereof to the copolymer and wherein the absence of such residual groups contribute to the low buffering capacity of the crosslinked copolymer. More importantly, the absence of active amino groups permits the coupling of aminosensitive ligands, such as the glycopeptide as heretofore described, to the chemically active sulfhydryl functional groups which would otherwise interact with and be inactivated by such amino groups when instead coupled thereto.

Preparation of Crosslinked Polyacrylamide-Sulfhydryl Copolymer

The present invention also provides a method for preparing the crosslinked polyacrylamide-sulfhydryl copolymer as heretofore described which comprises copolymerizing a mixture of monomers a' (bisacrylamide or analogs thereof), b' (acrylamide) and c' (N,N'-bisacrylylcystamine or analogs thereof) which correspond to their respective monomeric structural units a, b and c, respectively, as heretofore described. The crosslinked polyacrylamide-sulfhydryl copolymer so obtained can then be homogenized into discrete particles, preferably in the form of a gel slurry comprising discrete gel particles from between about 20 $\mu$m and 200 $\mu$m in diameter, more preferably from between about 38 $\mu$m and 150 $\mu$m in diameter, and reduced with a reducing agent such as dithiothreitol in order to generate the chemically active sulfhydryl functional groups as heretofore described.

Generally, the crosslinked copolymer is prepared by the free radical copolymerization of monomers a', b' and c' in water comprising a mixture from between about 1% and 12% of monomer a', from between about 32% and 48% of monomer b', and from between about 2% and 8% of monomer c' in the presence of N,N,N',N'-tetramethylethylenediamine and ammonium persulfate. The mixture is cooled in an ice bath and then allowed to polymerize into the form of a bulk polymer comprising a transparent, solid material. The bulk polymer so obtained is then homogenized with a mechanical blender or the like into the form of a water slurry comprising varying sizes of the crosslinked copolymer in the form of discrete gel particles from between about 20 $\mu$m and 200 $\mu$m in diameter. The desired sized particles, preferably from between about 38 $\mu$m and 150 $\mu$m in diameter, can then be separated with an appropriately meshed screen having a mesh size which corresponds to the size of the desired gel particle.

Preferably, the copolymerization mixture of monomers a', b' and c' comprises from between about 2% and 10% of monomer a', from between about 36% and 44% of monomer b', and from between about 3% and 7% of monomer c', in order to obtain a crosslinked copolymer which is substantially nonswellable in nonswelling liquid environments as heretofore described.

According to the preferred embodiments of the method of the present invention, m is 1 and n is 2 wherein the copolymerization reaction mixture comprises about 10% of monomer a', about 40% of monomer b' and about 3.4% of monomer c', or about 2% of monomer a', about 40% of monomer b', and about 6.8% of monomer c'. According to such preferred embodiments, monomer a' is bisacrylamide, monomer b' is acrylamide, and monomer c' is N,N'-bisacrylylcystamine.

It is to be appreciated that although the bulk copolymerization process as heretofore described is preferred to obtain the crosslinked polyacrylamide-sulfhydryl copolymer of the present invention, other polymerization processes including, but not necessarily limited to, suspension polymerization processes and the like can also be employed.

In particular, the present invention will now be illustrated, but is not intended to be limited, by the following examples:

EXAMPLE 1

Synthesis of Crosslinked Polyacrylamide-Sulfhydryl Copolymer Gel Particles

Under argon, acrylamide (40%), bisacrylamide (10%) and N,N'-bisacrylylcystamine (3.4%) were mixed with 30 ml of water. The temperature of the mixture was increased to 40° C.–45° C. in order to dissolve all of the solids. After 100 μl N,N,N',N'-tetramethylethylenediamine was added, the mixture was cooled to 40° C., and 25 mg ammonium persulfate was added and the solution was allowed to polymerize into the form of a bulk polymer in an ice bath. After 3 hours, the bulk polymer was removed from the vessel as a transparent, solid material and mixed with water and homogenized with a mechanical blender to obtain a gel suspension. The gel suspension was first sieved on a 85 mesh screen (USC Designation) to obtain gel particles having diameters less than 150 μm in diameter, which were then sieved on a 400 mesh screen to obtain particles from between 38 μm and 150 μm in diameter. The resulting 38 μm–150 μm particles were washed well with water, and the gel filtered and washed with ethanol and finally dried by suction and vacuum.

EXAMPLE 2

Preparation of Immobilized Glycopeptide Reagent

An immobilized reagent comprising a glycopeptide covalently bound to the external sulfhydryl functional groups of the crosslinked polyacrylamide-sulfhydryl gel particles prepared according to Example 1 was prepared as follows:

(a) 2.0 g of the crosslinked polyacrylamide-sulfhydryl copolymer gel particles prepared according to Example 1 was first washed (4 ×5 ml) with dimethylformamide (DMF), drained and mixed with 400 mg dithiothreitol (DTT) and 0.5 ml DMF. The mixture was stirred and vortexed occasionally at room temperature. After 1 hour, the liquid was drained and the gel was kept under argon and washed with argon-purged DMF until no DTT was detected from the wash.

(b) In a separate vessel, a 800 μl solution of a glycopeptide (the glucosylated N-terminal peptide sequence in the beta-subunit of hemoglobin as described in European patent application No. 185,870) at a concentration of 1.0 mg/100 μl water was mixed with a solution of 200 μl of bismaleimido-hexaethylene glycol (1.0 mg in 100 μl DMF) and 600 μl DMF. After 10 minutes at room temperature, the solution was added to the activated gel from step (a) of the present example. The gel mixture was stirred and vortexed occasionally for 2 hours. The gel was drained and washed with DMF (8×2 ml), a solution of 2 M NaCl and 0.1 N acetic acid (6×5 ml), water (150 ml) and ethanol (4 ×10 ml). The gel was then dried by suction and under vacuum to give 2.0 g of the immobilized glycopeptide reagent comprising the glycopeptide covalently bound substantially only to the external sulfhydryl functional groups of the crosslinked copolymer gel particle.

The covalent binding of the glycopeptide substantially only to the external surface sulfhydryl functional groups of the copolymer gel was determined by first activating the sulfhydryl functional groups with an excess amount of dithiothreitol (1.3 mM/gram gel) in dimethylformamide, according to the method described by Grassetti and Murray, *Archives of Biochemistry and Biophysics*, vol. 119, 44–49(1967). Approximately 10–500 nM of the sulfhydryl groups were detected per gram of the crosslinked polyacrylamide-sulfhydryl gel, or less than 0.05% of the available disulfide groups of the crosslinked copolymer prior to the reduction thereof. Accordingly, it is believed that substantially only the surface disulfide groups were exposed to the reducing reagent to result in the reduction of substantially only such disulfide groups to the desired external sulfhydryl functional groups.

EXAMPLE 3

Immobilized Glycopeptide Reagent Reactivity Assay

The immobilized glycopeptide reagent (resin) prepared according to Example 2 was evaluated to determine the level of unbound label (background) employing, as a labeled reagent, a monoconjugate preparation of a monovalent antibody fragment (Fab') labeled with β-D-galactosidase. The monovalent antibody fragment was derived from a monoclonal antibody specific for the glucosylated N-terminal peptide sequence in the beta-subunit of human hemoglobin (see European patent application No. 185,870) according to the methods described by Porter, *Biochem.J.*, Vol. 73, p. 119 (1959); and Nisonoff, *Methods Med. Res.*, Vol. 10, p. 132 (1964) and labeled with β-D-galactosidase according to the methods described by Ishikawa, *J. Biochem.*, Vol. 96, p. 659 (1984), Kato, et al., *J. Immunol.*, Vol. 116, p. 1554 (1976) and Yoshitake, et al., *Euro. J. Biochem.*, Vol. 101, p. 395 (1977). The monovalent antibody fragment-β-D-galactosidase conjugate was electrophoretically purified on a polyacrylamide gel to result in a substantially pure monoconjugate preparation comprising a single Fab' component and a single β-D-galactosidase component, as described in the copending U.S. patent application entitled "Substantially Pure Enzyme-Antibody Monoconjugate Preparation" (Docket No. MS-1477), filed on even date herewith.

(a) To a solution of 250 μl of the monoconjugate labeled reagent, 30 μl of buffer (pH 7.4, 0.05 M sodium phosphate, 0.05 M sodium chloride, 1 mM magnesium chloride, 100 μg/ml bovine serum albumin, and 0.02% sodium azide) was added;

(b) A 270 μl aliquot of the solution from step (a) of the present example was mixed with 10–20 mg of the immobilized glycopeptide reagent (resin) and the suspension was rotated end-over-end for 30 minutes at room temperature; and (c) The resin was removed by filtration and a 30 μl aliquot of the filtrate was applied to a reagent pad incorporated with resorufin-β-D-galactopyranoside.

The rate of color formation resulting from the interaction between the β-D-galactosidase and the resorufin-β-D-galactopyranoside was measured at 560 nM after the sample application to the reagent pad, in order to determine the β-D-galactosidase activity of the labeled reagent from the supernatant, i.e., the bound species. The reactivity measurements (Table 1) were made on a Seralyzer ® reflectance photometer (Miles Laboratories, Inc., Elkhart, IN, USA) attached to an HP-85 computer (Hewlett-Packard Company, Palo Alto, CA, USA) through a multiple port interface, and the ratio of the reactivity measured in this manner to the reactivity of the labeled reagent without the treatment of the resin were reported as background (see Table 1).

TABLE 1

| Immobilized Glycopeptide Reagent Sample # | Bismaleimido | Glycopeptide concentration | Reactivity | % Background |
|---|---|---|---|---|
| I | PEG-6 | 1 mg/g | 0.01801 | 48 |
| II | PEG-6 | 1 mg/g | 0.01992 | 62 |
| III | PEG-6 | 1 mg/g | 0.01655 | 59–64 |
| IV | PEG-6 | 2 mg/g | 0.02349 | 52.7 |
| V | PEG-6 | 4 mg/g | 0.01909 | 29.1 |
| VI | PEG-6 | 6 mg/g | 0.05032 | 76.7 |
| VII | methylene-diphenylene | 2 mg/g | 0.04202 | 89 |
| VIII* | PEG-6 | 2 mg/g | 0.06560 | 100 |
| IX** | PEG-6 | 1 mg/g | 0.05713 | 121 |

*Sequential addition of bismaleimido and glycopeptide
**Not activated by DTT

EXAMPLE 4

Immunoassay for the Determination of HbAlc (a) 30 μl of varying concentrations of denatured blood, i.e., HbAlc (FIG. 1), were added to 250 μl solutions of the labeled reagent (Example 3) and the mixtures allowed to stand for 10 minutes at room temperature;

(b) A 270 μl aliquot from each mixture was mixed with 15 mg of the immobilized glycopeptide reagent (Example 2) and rotated end-over-end for 10 minutes at room temperature; and (c) The resin was removed by filtration and 30 μl of the filtrate was applied to a reagent pad incorporated with resorufin-β-D-galactopyranoside.

The reactivity measurements were made with a Seralyzer® reflectance photometer as heretofore described and the reactivities were found to be directly proportional to the concentrations of HbAlc present in whole blood (see FIG. 1).

What is claimed is:

1. A method for preparing a water-insoluble crosslinked polyacrylamide polymer and immobilizing a biologically active substance thereon which comprises copolymerizing a mixture comprising monomers of the formulae:

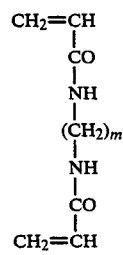

(a)

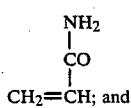

(b)

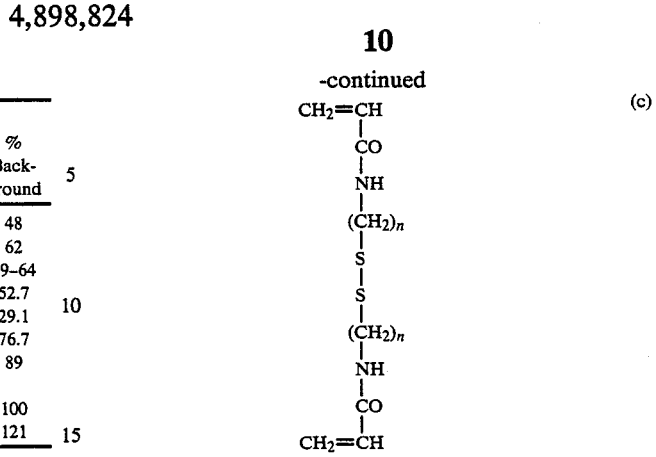

(c)

wherein m and n are, independently, integers from 1 through 6, and, isolating the resulting crosslinked polyacrylamide polymer, reducing said crosslinked polymer with a reducing agent to cleave the disulfide bond in the crosslinkages of monomer (c) to result in a crosslinked polymer free of residual amino and carboxylic acid groups and to form chemically active sulfhydryl groups, and reacting the reduced crosslinked polymer with a biologically active substance to couple said biologically active substance to said chemically active sulfhydryl group.

2. The method of claim 1 further comprising the step of homogenizing said crosslinked polymer into discrete particles.

3. The method of claim 1 wherein m is an integer from 1 through 3 and n is an integer from 2 through 4.

4. The method of claim 1 wherein m is 1 and n is 2.

5. The method of claim 1 wherein said mixture comprises an aqueous solution of from between about 1% and 12% of monomer (a), from between about 32% and 48% of monomer (b), and from between about 2% and 8% of monomer (c).

6. The method of claim 1 wherein said mixture comprises an aqueous solution of from between about 2% and 10% of monomer (a), from between about 36% and 44% of monomer (b), and from between about 3% and 7% of monomer (c).

7. The method of claim 4 wherein said mixture comprises an aqueous solution of about 10% of monomer (a), about 40% of monomer (b), and about 3.4% of monomer (c).

8. The method of claim 4 wherein the reaction mixture comprises an aqueous solution of about 2% of monomer (a), about 40% of monomer (b), and about 6.8% of monomer (c).

9. The method of claim 2 wherein said discrete particles are from between about 20 μm and 200 μm in diameter.

10. The method of claim 2 wherein said discrete particles are from between about 38 μm and 150 μm in diameter.

11. The method of claim 9 wherein said particles are discrete gel particles.

12. A water insoluble crosslinked polyacrylamide polymer containing an immobilized biological active substance prepared by the method of claim 1.

* * * * *